United States Patent [19]

Karrenbauer et al.

[11] Patent Number: 4,772,749
[45] Date of Patent: Sep. 20, 1988

[54] PROCESS FOR THE RECOVERY OF MALIC ACID

[75] Inventors: Michael Karrenbauer, Rodenbach; Axel Kleemann, Hanau; Wolfgang Leuchtenberger, Bruchköbel; Rudi Moerck, Gelnhausen-Meerholz, all of Fed. Rep. of Germany

[73] Assignee: Degussa Aktiengesellschaft, Frankfurt am Main, Fed. Rep. of Germany

[21] Appl. No.: 563,983

[22] Filed: Dec. 21, 1983

[30] Foreign Application Priority Data

Dec. 24, 1982 [DE] Fed. Rep. of Germany ....... 3247981

[51] Int. Cl.$^4$ .............................................. C07C 51/42
[52] U.S. Cl. .................................... 562/580; 562/582; 435/145
[58] Field of Search ................. 562/580, 582; 435/145; 560/180

[56] References Cited

U.S. PATENT DOCUMENTS

| | | | |
|---|---|---|---|
| 3,371,112 | 2/1968 | Winstrom et al. | 562/580 |
| 3,922,195 | 11/1975 | Chibata et al. | 435/145 |
| 4,304,858 | 12/1981 | Wandrey et al. | 435/115 |

FOREIGN PATENT DOCUMENTS

| | | | |
|---|---|---|---|
| 1543977 | 7/1975 | Fed. Rep. of Germany . | |
| 2930070 | 2/1981 | Fed. Rep. of Germany | 435/115 |
| 1290312 | 3/1962 | France . | |
| 2033892 | 5/1980 | United Kingdom | 562/580 |

Primary Examiner—Michael L. Shippen
Assistant Examiner—Bruce D. Gray
Attorney, Agent, or Firm—Cushman, Darby and Cushman

[57] ABSTRACT

The reaction mixture obtained in the enzymatic reaction of fumaric acid to form L-malic acid contains the L-malic acid and unreacted fumaric acid as their salts. To recover pure solutions of L-malic acid the reaction mixture is treated at 50° to 150° C. with cation exchangers. The eluate after concentration to 30 to 80 weight % content of L-malic acid is filtered. The pure L-malic acid is recovered by evaporating the solutions, in a given case after treatment with activated carbon.

24 Claims, No Drawings

PROCESS FOR THE RECOVERY OF MALIC ACID

BACKGROUND OF THE INVENTION

The invention is directed to a process using ion exchangers for obtaining L-malic acid from the reaction mixtures resulting from the enzymatic reaction of fumaric acid to form L-malic acid.

It is known to produce L-malic acid by enzymatic reaction of fumaric acid, namely the fumaric acid is generally employed as a salt in aqueous solution so that the resulting reaction mixtures contain the malic acid and unreacted fumaric acid as their salts. Besides it is known to obtain pure L-malic acid from these reaction mixtures by first separating off the unreacted fumaric acid by acidification, then separating off the L-malic acid as the calcium salt in the form of dihydrate, then dissolving this salt by means of sulfuric acid, successively leading the solution over an acid ion exchanger and base ion exchanger for the purpose of removal of the calcium and sulfate ions and finally separating off the malic acid (German No. OS 2450137, the entire disclosure of which is hereby incorporated by reference and relied upon). The process is cumbersome and expensive and the yield of L-malic acid is unsatisfactory.

SUMMARY OF THE INVENTION

There has now been developed a process using an ion exchanger for obtaining a pure, aqueous solution of L-malic acid from the reaction mixture resulting from the enzymatic reaction of fumaric acid to form L-malic acid which is characterized by (a) treating the reaction mixture at a temperature between about 50° and 150° C. with a cation exchanger and (b) after concentration of the eluate to 30 to 80 weight % content of L-malic acid filtering it. Hereby there is obtained an aqueous solution of very pure L-malic acid in outstanding yields in a few simple steps.

The process of the invention is suitable for obtaining pure aqueous solutions of L-malic acid from the reaction mixtures which are obtained in the customary reactions of a Fumarase enzyme with the salts of fumaric acid. Typical examples of salts are sodium fumarate, potassium fumarate and ammonium fumarate. The Fumarase enzyme typically can be produced from microorganisms such as those mentioned in German No. OS 2450137, e.g. *Brevibacterium ammoniagens* IAM 1461, *Brevibacterium ammoniagens* IAM 1645, *Corynebacterium equi* IAM 1038, *Escherichia coli* ATCC 11303, *Microbacterium flavum* IAM 1642, *Pichia farinosa* IFO 0574 and *Proteus vulgaris* IFO 3045.

The reaction mixture generally contains about 5 to 15 weight % of the salt of L-malic acid.

To carry out the process of the invention the reaction mixture after separation of the enzymes and the possible undissolved components is treated with a cation exchanger, e.g. a cation exchange resin. As the cation exchanger there is employed a conventional acidic, preferably a strongly acidic ion-exchanger, for example of polystyrene, or styrene-divinylbenzene based resin or other crosslinked styrene polymer containing acid groups, especially such a polymer containing free sulfonic acid groups, e.g. sulfonated styrene-divinyl benzene copolymer.

The treatment with the cation exchanger is carried out at a temperature between about 50° and 150° C., preferably between 70° and 120° C. especially between 70° and 90° C. Hereby the pressure can be chosen in a wide range as desired. However, it is generally suitable to select a pressure which is between normal pressure and a pressure up to 3 bar, preferably up to 1 bar over the vapor pressure of the liquid at the treatment temperature used.

Per mole of salt of fumaric acid employed there is used at least two equivalents, suitably 2.5 to 3.0 equivalents of the cation exchanger. The regeneration of the ion exchanger is carried out with a strong acid, preferably a strong mineral acid, e.g. sulfuric acid, and especially with concentrated aqueous hydrochloric acid.

The eluate remaining after the treatment with the cation exchanger is concentrated to such an extent by evaporation of water that the content of L-malic acid is about 30 to 80 weight %, preferably 50 to 60 weight %.

The evaporation of water is carried out suitably at reduced pressure at temperature up to about 80° C. The thus concentrated solution is filtered at a temperature of about 0° to 20° C.

The filtrate is a pure aqueous solution of L-malic acid. This solution can be directly employed for several purposes of use. The pure L-malic acid can be separated from the solution by further evaporation, preferably under reduced pressure, in a given case by evaporation to dryness.

In those cases where an especially pure L-malic acid is needed, it is advantageous to treat the solution remaining after filtration with activated carbon. Per liter of solution there is suitably used 5 to 100 grams, preferably 10 to 30 grams, of activated carbon.

Unless otherwise indicated all parts and percentages are by weight.

The process can comprise, consist essentially of or consist of the steps recited with the stated materials.

DETAILED DESCRIPTION

Examples

The L-malic acid obtained in each case was investigated as to its specific rotation $[\alpha]_D^{20}$, C=5.5 in pyridine. This is stated in degrees $\times cm^3/dm \times$ grams. Percent data are weight percent.

Example 1

There was used a reaction mixture which was obtained in the reaction of a solution of 96 grams of the sodium salt of fumaric acid in 600 ml of water by means of fumarase according to the ultrafiltration process of German No. OS 2930070, the entire disclosure of which is hereby incorporated by reference and relied upon. The reaction mixture contained 67.3 grams of the sodium salt of the L-malic acid as well as 35.5 grams of unreacted sodium salt of fumaric acid. It was heated to 85° C. and at this temperature in the course of 60 minutes passed over an exchange column having a diameter of 5.5 cm and a height of 50 cm and heated to 85° C. The column contained 1000 ml of a strongly acid cation exchanger (Lewatit S100, H+ form, a sulfonated styrene-divinylbenzene resin). The usable capacity of the exchanger corresponds to 1.8 val of hydrogen ions. The eluate was evaporated at 70° C. and 100 mbar until the concentration of L-malic acid increased to 32% and then was cooled to 15° C. in the course of 60 minutes. Hereby there separated off fumaric acid. This was filtered off. (It was converted into its sodium salt by means of sodium hydroxide and reused as a further starting material.) The filtrate contained 49.6 grams of L-malic acid, corresponding to 98% yield, based on the L-malic acid which was contained in the reaction mixture. The thus obtained L-malic acid solution contained 0.13% fumaric acid, 1.5 ppm iron, 4.5 ppm sodium, less than 100 ppm chloride and less than 100 ppm sulfate. The solution was treated with 7.5 grams of low iron activated carbon (Eponit 113 Spezial). The mixture was held at 60° C. for 60 minutes with stirring and the filtered at this temperature. The filtrate was evaporated to dryness at 60° C. and 15 mbar. Hereby there were obtained 49.1 grams of L-malic acid, corresponding to a yield of 97%, based on the L-malic acid which was contained in the reaction mixture. The L-malic acid was colorless. It contained 0.09% fumaric acid, 5 ppm iron, 140 ppm sodium, less than 100 ppm chloride and less than 100 ppm sulfate. Its melting point was 102° to 104° C., its rotary value −28.8°.

Example 2

The procedure was as in Example 1 but the eluate was evaporated to the extent that the content of L-malic acid increased to 56% and it was then filtered at 4° C. The filtrate contained 48.7 grams of L-malic acid, corresponding to 96% yield, as well as 0.06% fumaric acid, 2 ppm iron, 22 ppm sodium, less than 100 ppm chloride and less than 100 ppm sulfate. By evaporating the solution to dryness there were obtained 48.6 grams of L-malic acid, corresponding to a yield of 96%. The malic acid contained 0.11% fumaric acid, 4 ppm iron, 40 ppm sodium, less than 100 ppm chloride and less than 100 ppm sulfate. Its melting point was 103° C., its rotary value −28.8°.

Example 3

The procedure was as in Example 1 but after the treatment with the cation exchanger (Duolite C 26, H+ form, sulfonated styrene-divinylbenzene resin) the mixture was evaporated to the extent that the content of L-malic acid increased to 65% and after cooling in the course of 12 hours it was filtered at 0° C. The filtrate contained 47.4 grams of L-malic acid, corresponding to a yield of 94%, as well as 0.04% fumaric acid, 2 ppm iron, 15 ppm sodium, less than 100 ppm chloride and less than 100 ppm sulfate.

Example 4

The procedure was as in Example 1 but after the treatment with the cation exchanger (Duolite C 26, H+ form) the mixture was evaporated until the L-malic acid content increased to 55% and after cooling in the course of 4 hours was filtered at 15° C. The filtrate contained 49.3 grams of L-malic acid, corresponding to a yield of 97%, as well as 0.2% fumaric acid, 3 ppm iron, 30 ppm sodium, less than 100 ppm chloride and less than 100 ppm sulfate. The malic acid solution was treated with 8.0 grams of activated carbon (Eponit 114 Spezial). The mixure was held at 25° C. under stirring for 60 minutes and then filtered. The filtrate was evaporated to dryness at 60° C. and 40 mbar. Hereby there were obtained 49.1 grams of L-malic acid, corresponding to a yield of 97%. The malic acid contained 0.08% fumaric acid, 6 ppm iron, 55 ppm sodium, less than 100 ppm chloride and less than 100 ppm sulfate. Its melting point was 101° to 103° C., its rotary value −29.1°.

Example 5

There was employed as the starting reaction mixture one which was obtained in the reaction of 90 grams of the ammonium salt of fumaric acid in 600 ml of water according to the untrafiltration process. The reaction mixture contained 63.5 grams of the ammonium salt of L-malic acid and 33.3 grams of the ammonium salt of fumaric acid. The treatment with the cation exchanger (Duolite C 26 H+ form) was carried out at 85° C. The eluate was evaporated at 70° C. and 100 mbar until the content of L-malic acid was 55% and then in the course of 4 hours it was cooled to 15° C. The solution remaining after the separation of the fumaric acid contained 49.1 grams of L-malic acid, corresponding to a yield of 97.0%, 0.2% fumaric acid and 15 ppm ammonium. It was treated with 10 grams of activated carbon (Eponit 114 Spezial), stirred at 25° C. for 60 minutes, filtered and then evaporated to dryness at 60° C. and 40 mbar. There were obtained 49.0 grams of L-malic acid, corresponding to a yield of 96.7%. It contained 0.09% fumaric acid and 32 ppm ammonium. Its melting point was 101° to 103° C., its rotary value −29.1°.

Example 6

There was employed as the starting reaction mixture one which was obtained in the reaction of 115 grams of the potassium salt of fumaric acid in 600 ml of water according to the ultrafiltration process. The reaction mixture contained 79.4 grams of the potassium salt of L-malic acid and 42.7 grams of the potassium salt of fumaric acid. Otherwise the procedure was as in Example 5. The L-malic acid solution obtained contained 49.4 grams of L-malic acid, corresponding to a yield of 97.5%, 0.22% of fumaric acid and 20 ppm potassium. The yield of L-malic acid was 49.3 grams, corresponding to 97.3%. The malic acid contained 0.1% fumaric acid and 40 ppm potassium. Its melting point was 102° to 103° C., its rotary value −29.1°.

Example 7

There was used a reaction mixture which was obtained in the reaction of 96 grams of the sodium salt of fumaric acid in 600 ml of water by means of immobilized fumarase. The reaction mixture contained 74.8 grams of the sodium salt of L-malic acid as well as 28.8 grams of the sodium salt of fumaric acid. It was passed over 900 ml of cation enchanger (Duolite C 26 H+ form) in the course of 80 minutes at 70° C. The eluate was evaporated at 60° C. and 50 mbar until the content of L-malic acid was 50% and then it was cooled to 15° C. in the course of 60 minutes. The solution remaining after filtering off the fumaric acid contained 54.6 grams of L-malic acid, corresponding to 97% yield, 0.19% fumaric acid, 3 ppm iron, 40 ppm sodium less than 100 ppm chloride and less than 100 ppm sulfate. It was evaporated to dryness at 60° C. and 50 mbar. There were obtained 54.6 grams of L-malic acid, corresponding to a yield of 97%. The L-malic acid contained 0.39% fumaric acid, 5 ppm iron, 80 ppm sodium and chloride and sulfate in each case less than 100 ppm. Its melting point was 102° to 104° C., its rotary value −28.8°.

Example 8

The procedure was as in Example 7 but there was employed as the reaction mixture one which was obtained in the reaction of 160 grams of the sodium salt of fumaric acid in 1000 ml of water by means of immobilized fumarase and contained 143.8 grams of the sodium salt of malic acid and 30.8 grams of the sodium salt of fumaric acid. The reaction mixture was passed over 1700 ml of the ion exchanger at 55° C. There was obtained a solution which contained 106 grams of L-malic acid, corresponding to 98% yield, 0.2% fumaric acid, 2 ppm iron, and 40 ppm sodium.

Example 9

The procedure was as in Example 7 but the reaction mixture was passed over 1200 ml of the cation exchanger at 120° C. and 1.0 bar superatmospheric pressure (gauge pressure) in the course of 60 minutes. The solution obtained contained 54.0 grams of L-malic acid, corresponding to a yield of 96%, 0.18% fumaric acid, 4 ppm iron and 35 ppm sodium. In the evaporation of the solution to dryness there were obtained 53.9 grams of L-malic acid, corresponding to a yield of 96%. This contained 0.36% fumaric acid, 7 ppm iron and 70 ppm sodium. Its melting point was 103° to 104° C., its rotary value −28.8°.

What is claimed is:

1. A process for the recovery of a pure aqueous solution of L-malic acid from the reaction mixture obtained in the enzymatic reaction of fumaric acid to L-malic acid, the reaction mixture containing as the only salts of fumaric acid and L-malic acid a member of the group consisting of sodium fumarate, potassium fumarate and ammonium fumarate and a corresponding member of the group consisting of sodium L-malate, potassium L-malate and ammonium L-malate, comprising heating the aqueous reaction mixture at a temperature between about 50° and 150° C. with a cation exchanger, and concentrating the eluate to between 30 and 80 weight % of L-malic acid and filtering to remove solids.

2. A process according to claim 1 wherein the cation exchanger is a sulfonated resin.

3. A process according to claim 2 wherein the sulfonated resin is a sulfonated cross-linked styrene resin.

4. A process according to claim 1 wherein the reaction mixture employed contained 5 to 15% of a water soluble salt of L-malic acid.

5. A procss according to claim 4 wherein the water soluble salt is the potassium, sodium or ammonium salt.

6. A process according to claim 5 wherein the temperature during the cation exchanger treatment is 70° to 120° C.

7. A process according to claim 5 wherein the temperature during the cation exchanger treatment is 70° to 90° C.

8. A process according to claim 6 wherein there are used at least two equivalents of the cation exchanger per mole of the salt of fumaric acid employed.

9. A process according to claim 8 wherein there are used 2.5 to 3.0 equivalents of the cation exchanger per mole of the salt of fumaric acid employed.

10. A process according to claim 1 wherein the eluate is concentrated to 50 to 60 weight % of L-malic acid.

11. A process according to claim 10 wherein the cation exchanger is a sulfonated crosslinked styrene resin.

12. A process according to claim 11 wherein after the filtration the eluate is treated with activated carbon.

13. A process according to claim 1 wherein after the filtration the eluate is treated with activated carbon.

14. A process according to claim 1 wherein the cation exchanger treatment is the sole ion exchange treatment.

15. A process according to claim 5 wherein the cation exchanger treatment is the sole ion exchange treatment.

16. A process according to claim 1 consisting essentially of heating the aqueous reaction mixture at a temperature between about 50° and 150° C. with a cation exchanger and concentrating the eluate to 30 to 80 weight % of L-malic acid and filtering to remove solids.

17. A process according to claim 5 consisting essentially of heating the aqueous reaction mixture at a temperature between about 50° and 150° C. with a cation exchanger and concentrating the eluate to 30 to 80 weight % of L-malic acid and filtering to remove solids.

18. A process according to claim 1 consisting of heating the aqueous reaction mixture at a temperature between about 50° and 150° C. with a cation exchanger and concentrating the eluate to 30 to 80 weight % of L-malic acid and filtering to remove solids.

19. A process according to claim 5 consisting of heating the aqueous reaction mixture at a temperature between 50° and 150° C. with a cation exchanger and concentrating the eluate to 30 to 80 weight % of L-malic acid and filtering to remove solids.

20. A process according to claim 1 wherein the reaction mixture contains the L-malic acid and the fumaric acid in the form of a water soluble salt.

21. A process according to claim 1 which the sole salts of fumaric acid and L-malic acid present are sodium fumarate and sodium L-malate.

22. A process according to claim 1 which the sole salts of fumaric acid and L-malic acid present are potassium fumarate and ammonium L-malate.

23. A process according to claim 1 which the sole salts of fumaric acid and L-malic acid present are ammonium furmarate and ammonium L-malate.

24. A process according to claim 1 wherein there is absorbed on the cation exchanger the sodium, potassium or ammonium ions, said ions being the only ions absorbed on the resin.

* * * * *